United States Patent [19]
Thornton

[11] 3,984,766
[45] Oct. 5, 1976

[54] DIGITAL APPARATUS FOR RAPIDLY DETECTING THE GROWTH OF AND IDENTIFYING MICRO-BIOLOGICAL ORGANISMS

[75] Inventor: Douglas D. Thornton, Oakland, Calif.

[73] Assignee: Bactomatic Inc., Palo Alto, Calif.

[22] Filed: Oct. 15, 1974

[21] Appl. No.: 514,294

[52] U.S. Cl. ............................ 324/57 R; 324/61 R; 324/65 R
[51] Int. Cl.² ....................................... G01R 27/00
[58] Field of Search .............. 324/57 R, 60 R, 61 R, 324/62, 65 R; 195/103.5 R

[56] References Cited
UNITED STATES PATENTS

| | | | |
|---|---|---|---|
| 2,817,810 | 12/1957 | Sontheimer | 324/60 R X |
| 3,443,215 | 5/1969 | Bradley | 324/57 R |
| 3,490,039 | 1/1970 | Tsao | 324/62 |
| 3,652,930 | 3/1972 | Sugiyama | 324/57 R |
| 3,743,581 | 7/1973 | Cady et al. | 195/103.5 R |
| 3,784,906 | 1/1974 | Ironside | 324/62 |
| 3,836,847 | 9/1974 | Lucas | 324/62 |

*Primary Examiner*—Stanley T. Krawczewicz
*Attorney, Agent, or Firm*—Phillips, Moore, Weissenberger, Lempio & Strabala

[57] ABSTRACT

Digital apparatus is disclosed which provides means for plotting the change with respect to time in the impedance ratio between a pair of cells, both cells of the cell pair containing a selected nutrient media and one (specimen) cell of the cell pair further including a micro-organism contaminant the growth of which is to be detected. Growth of the contaminant within the specimen cell over a selected period of time provides a characteristic change in the impedance of the specimen cell which provides, in turn, a corresponding change in the impedance ratio between the cells of the cell pair. Measurements are digitally made via means which compares the impedance ratio between the cells of the cell pair to successive resistive approximations of the ratio, and then outputs a digital word corresponding to the nearest approximation. Each digital word thus represents the impedance ratio at a given point in time of growth. At least a portion of the digital word or an arbitrary value indicative thereof is recorded with respect to time, for example, by electromagnetic means or as one point on a strip chart. Thus, a characteristic record is produced of the change with respect to time in the impedance ratio between the pair of cells caused by the particular micro-organism contaminant as it grows within the specific nutrient media of that pair of cells.

A plurality of cell pairs with both cells of each pair containing a nutrient media different from that in the other cell pairs and with the specimen cell of each pair containing the same micro-organism contaminant, may be sequentially and repeatedly sampled via the digital apparatus of the invention during a given period of time, wherein successive impedance ratios characteristic of contaminant growth in each media during such period of time are recorded. The combined record during such period of time defines a "signature" which is peculiar to the contaminant and comparisons of the "signature" with known "signatures" allows rapid identification of the contaminant.

21 Claims, 8 Drawing Figures

FIG_1

FIG_2

FIG. 3

FIG_6

FIG_7

(A) START
(B) ONE-SHOT 52
(C) ONE-SHOT 54
(D) ONE-SHOT 50
(E) SHIFT REGISTERS 57,58

FIG_8

DIGITAL APPARATUS FOR RAPIDLY DETECTING THE GROWTH OF AND IDENTIFYING MICRO-BIOLOGICAL ORGANISMS

BACKGROUND OF THE INVENTION

1. Field

The present invention relates to apparatus for rapidly detecting the growth of a micro-biological organism within a selected nutrient media by measuring and recording a succession of changes in the electrical impedance of a small quantity thereof, and more particularly to such apparatus capable of digitally measuring and recording a succession of changes in the electrical impedance of a large number of samples differing from each other in either the organism or the nutrient media involved or both.

2. Prior Art

Heretofore, the usual procedure for identifying the presence and extent of a micro-biological organism, given a biological, medical, food, soil, sewage, etc., sample, has been to introduce the unknown microorganism into a selected nutrient media to allow growth of the former. It is not unusual for days to elapse before the growth proceeds to the state where positive counting and identification of the microbial specimen can be performed. In fact, it is not unusual to culture a specimen for a week to several weeks in order to provide a positive identification and a quantitative analysis. Obviously, as in the case of medical diagnosis, such long delays are a decided handicap to a physician who accordingly may have to prescribe medical treatment for a patient without having early access to the positive identification of the micro-biological organism.

U.S. Pat. No. 3,743,581, issued to Paxton Cady and William J. Welch on July 3, 1973, teaches a novel method of and means for electrically measuring the growth of a micro-biological organism. The measurements are made by sampling the ratio of the voltages across two cells, one cell containing a nutrient media and being the "reference" cell, the other cell containing the same nutrient media innoculated with the subject micro-biological organism, and being the "specimen" cell. The cells define two legs of a current nulling bridge network of the Wheatstone type and the measurements are made by simple analog circuits.

Thus, the apparatus disclosed in U.S. Pat. No. 3,743,581 for practicing the novel method taught therein requires an operator to repeatedly balance the bridge circuit and read the measurements therefrom at different points in time for recording. In order to obtain useful results from such apparatus, it is necessary that the operator thereof possess a high degree of skill. Furthermore, any attempt to automate the operation of the apparatus is complicated by the relatively high sensitivity required of the apparatus for detection of the minute changes in the ratio of the voltages between the cells caused by growth of a micro-biological organism.

It is an object of this invention to provide apparatus for practicing the method taught in U.S. Pat. No. 3,743,581 capable of automatically producing a digital output representative of the ratio of voltages between a pair of cells at a given point in time with a high degree of accuracy.

It will be understood that efficient use of apparatus of this type requires that it be capable of measuring the voltage ratios of large numbers of cell pairs. in some cases all of the cell pairs will contain the same nutrient media with the specimen cell of each pair containing a different micro-biological organism, in other cases each of the cell pairs will contain a different nutrient media with the specimen cells of all of the cell pairs containing the same micro-biological organism and, finally, both the nutrient media and the micro-biological organism may be different in each cell pair of a plurality of cell pairs in certain applications. The wide differences in the amount of change produced by different micro-biological organisms in different nutrient mediae requires increased skill on the part of the operator of the prior art apparatus whereas the mere quantity of the readings required will tend to produce errors caused by fatigue and impose a maximum limit on the number of cell pairs that can be monitored.

It is another object of this invention to provide apparatus which is capable of automatically producing digital outputs each representative of the ratio of voltages between a different one of a large number of cell pairs with a high degree of accuracy and in a small amount of time and to do so repeatedly over an extended period of time.

In order to identify a particular micro-biological organism it is necessary to study the growth thereof in a large number of different nutrient media with and without specific antisera which inhibit or support growth of different micro-biological organisms. The resultant measurements of the voltage ratios between each of a large number of cell pairs made repeatedly over an extended period of time must be recorded in a manner which will enable them to be studied with respect to each other in order to arrive at an accurate identification. According to the prior art, the readings of the operator were recorded manually and subsequently manually processed with additional opportunity for error to produce a graphical presentation for study.

It is a further object of this invention to provide apparatus which is capable of automatically producing digital outputs each representative of the ratio of voltages between a different one of a large number of cell pairs which outputs can be conveniently recorded and compared to each other to provide early and accurate comparison therebetween.

SUMMARY OF THE INVENTION

Briefly, apparatus according to this invention comprises means for supplying an electrical reference signal connected across two series connected impedances such as a pair of cells including a reference cell and specimen cell, each of which contains a sample of the same nutrient media while the specimen cell further contains a selected micro-organism contaminant. Each of the cells includes a pair of spaced electrodes in galvanic contact with the nutrient media contained therein with one electrode of each cell electrically connected to one electrode of the other cell and the other electrode of each cell connected to a different one of the terminals of the means for supplying the electrical reference signal. A sensor means is connected across the means for supplying the electrical reference signal in parallel with the series connected impedance elements or cells and includes means connected to the junction between the cells for generating a digital word representative of the electrical impedance ratio of the cells with respect to each other. A means for recording at least a portion of such digital word or an arbitrary value indicative thereof with respect to time is provided. A plurality of cell pairs may be connected in parallel across the means for supplying the electrical reference signal with the respective junctions therebetween being sequentially connected to the sensor means. The recording means may comprise a strip chart with longitudinal sectors thereof each for recording values representative of the various digital words generated at the junction between a different pair of the plurality of cell pairs in order to provide a combined chart constituting a visual signature for a particular set of test parameters for micro-organism growth.

BRIEF DESCRIPTION OF THE DRAWINGS

FIG. 3 is a representation of a strip chart type presentation of data according to a preferred embodiment of this invention particularly suited for providing a micro-organism "signature" in visual form.

DESCRIPTION OF THE PREFERRED EMBODIMENTS

Figure 1:
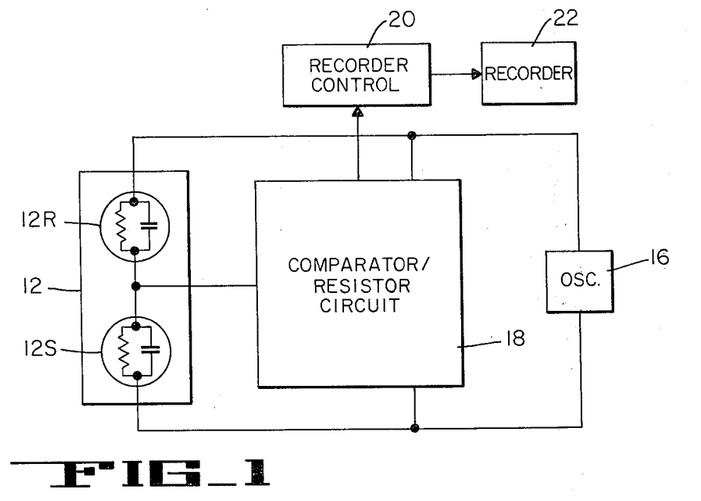
FIGS. 1 and 2 are block diagrams of the inventive combination.

FIG. 1 depicts the basic elements of the inventive apparatus, wherein a cell pair 12 includes a reference cell 12R and a specimen cell 12S, serially connected across a source of alternating current, e.g., oscillator 16. Comparator/resistor (sensor) circuit 18 is connected in parallel with the cells 12R, 12S across the output of oscillator 16, and to the junction of the cells to provide logic for making impedance ratio approximations, while performing in essence an analog-to-digital function. The circuit 18 provides a digital word output to recorder control means 20, which word is indicative of the impedance ratio between the cells. The recorder control means 20 introduces the digital word or an output representative thereof to a recorder means 22 adding the timing required to record the data with respect to time.

For example, in a preferred embodiment of this invention the recorder control means 20 converts the digital word, or a portion thereof, to a voltage representative of the cell pair impedance ratio and introduces such voltage to a recorder 22 in the form of a strip chart recorder. As growth of the organism continues in the nutrient media, a series of impedance ratios are taken, each via the digital approximation process. The impedance ratios are recorded against time as a series of voltage values by the strip chart recorder to define a continuous graph. The latter is characteristic of the rate and degree of growth of the particular organism/media combination.

If the changes in the impedance ratios of unknown micro-biological organisms are taken over a selected period of time of a relatively few hours, in several different nutrient mediae, a like plurality of curves each characteristic of a specific organism/media combination are obtained. (See FIG. 3). These curves constitute a "signature" which may be compared to graphical data previously prepared by growth of known quantities and types of micro-organisms in combination with identical nutrient mediae, to thus provide ready identification of the various organisms.

Figure 2:
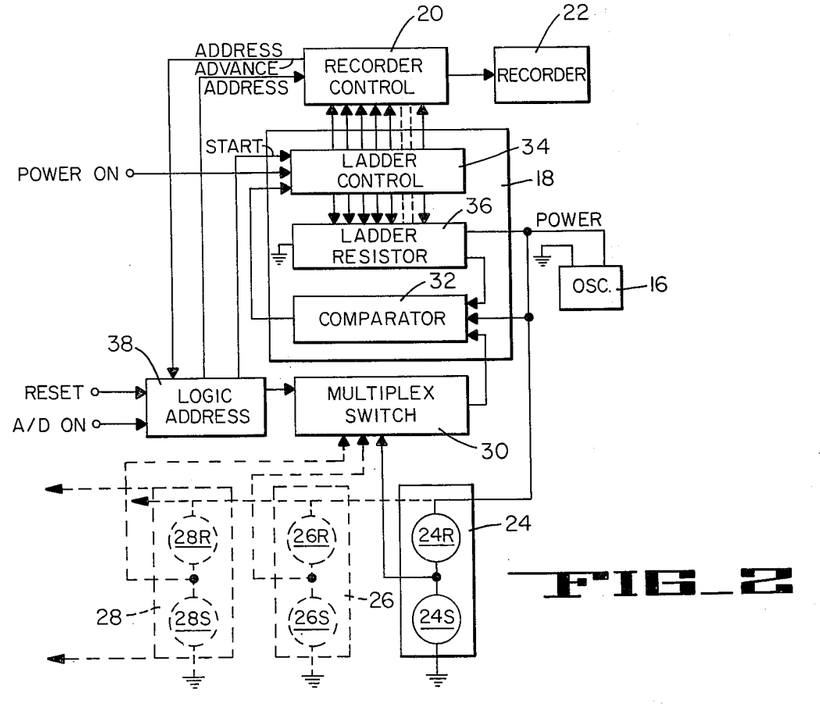

Referring to FIG. 2, the inventive apparatus is shown in further detail. It will be understood that the single cell pair 12 shown in FIG. 1 comprises a plurality of cell pairs 24, 26, 28, . . . , etc., according to the embodiment of FIG. 2, each of which is individually and selectively coupled to the sensor (comparator/resistor) circuit 18 via multiplex switch means 30. Although only three cell pairs are shown herein by way of example, any number may be employed. In an actual embodiment of apparatus according to this invention we have found the use of modules of eight cell pairs each to be convenient, with the apparatus being designed to accept up to eight modules or 64 cell pairs.

In particular, the sensor circuit 18 comprises comparator means 32, ladder control means 34 and ladder resistor means 36. The junction between the cells of cell pairs 24 through 28 are selectively coupled to comparator means 32 of the sensor circuit 18 through the multiplex switch 30. The oscillator 16 provides a power input at a given voltage to the ladder resistor means 36 and to all of the cell pairs 24-28 in parallel with each other. Thus, a fraction of the voltage provided by the oscillator 16 will be present between the cells of each cell pair with the value of the fraction directly related to the ratio of the impedance of the cells of each cell pair.

The output of the ladder resistor means 36 is also connected to the comparator means 32. The function of the ladder resistor means 36 is to supply to the comparator means 32 a series of fractions of the voltage provided by the oscillator 16 for comparison with that present at the junction between the cells of the cell pair 24-28 selected by the multiplex switch 30.

The output from the comparator means 32 is connected to the ladder control means 34, which is adapted to generate a feedback control signal to the ladder resistor means 36 in the form of a series of digital words which cause the ladder resistor means 36 to step through a series of fractions of the oscillator 16 voltage, differing from each other by small increments, until the output of the comparator represents a voltage difference between that supplied by the ladder resistor means 36 and that present at the junction between the cells of the selected pair of cells 24-28 which is less than such increments.

The ladder control means 34 also supplies the digital words representative of the fractional voltage produced by the ladder resistor means 36 which most nearly approximates that present at the junction between the cells of the selected pair to the recorder control 20 for introduction to the recorder 22. At the same time, a logic address circuit 38 connected to the multiplex switch 30, presents an identifying ADDRESS signal to the recorder control 20 for recording to identify the particular cell pair connected to the comparator means by the switch 30. When the recording process is complete, the recorder control supplies an address advance signal to the logic address circuit 38 which causes the multiplex switch 30 to couple the next cell pair to the comparator 32. The logic address circuit 38 also sends a START signal to the ladder control means 34 to restart its function of causing the ladder resistor means 36 to step through its series of fractions of the given voltage of the oscillator 16.

A POWER ON signal is fed to the ladder control means 34 from a front panel switch (not shown) when the power supply (not shown) for the apparatus is turned on to ready the apparatus for operation. Similarly, an A/D ON signal is supplied to the logic address cirucit 38 by appropriate means (not shown) to indicate that the sensor circuit 18 is ready for operation and a RESET signal may be applied to the logic address circuit 38 by manually operable means (not shown) to cause it to regenerate the START signal thereby interrupting and restarting the operation of the apparatus with respect to a given cell pair.

Referring to FIG. 3, an example is shown of the "signature" type graphic output which may be obtained from apparatus in accordance with a preferred embodiment of the teaching of this invention when the recorder 22 is a strip chart recorder. The graph as shown in FIG. 3 is divided into sixteen horizontally extending sectors, one for each of sixteen cell pairs provided by two modules of eight cell pairs each. Such sectors are numbered from 1 to 16 at the left hand side of FIG. 3.

Within each sector the change in the impedance ratio between the cells of a different cell pair is shown on the ordinate against time in hours, for example, on the abscissa which is common to all sectors. Thus, it will be seen that the change in impedance ratio between the cells of cell pairs 1, 2, 4, 5, 8, 9, 10, 12 and 16 during the time period involved is small, resulting in relatively smooth substantially continuous curves. However, the change in impedance ratio between the cells of cell pairs 3, 6, 7, 11, 13, 14 and 15, as shown in FIG. 3, is quite radical resulting in the curves each being broken into a plurality of portions each extending the full height of the sector assigned to the particular cell pair involved.

It will be understood that, at time zero, the impedance of the cells of each cell pair will be substantially equal (or, differently stated, the ratio of the impedance of each cell of a cell pair to the total impedance of such cell pair will be substantially ½). In any event, substantially one-half of the given voltage of the oscillator 16 will be developed across each of the cells of each cell pair at time zero.

We have found that the most common effect of micro-bioligical organisms in the specimen cell of a cell pair is to decrease the impedance thereof with respect to the reference cell, thus increasing the ratio of the impedance of the reference cell to the total impedance of the cell pair toward unity. For this reason the ratio of the impedance of the reference cell to the total impedance of the cell pair has been chosen for plotting on the ordinate of the graph of FIG. 3 in order to provide positive values in the majority of samples.

At this point, it must be understood that the impedance changes caused by the metabolic processes of the micro-organisms in the specimen cell are not very large, even after extended periods of time, and in order to detect the change in impedance which occurs in a matter of ten minutes or so due to such metabolic processes, the apparatus must be extremely sensitive. Thus, impedance changes which may occur due to mere settling or ageing of the nutrient media must be balanced out through the use of cell pairs and minute voltage changes which occur even in the most carefully regulated power supplier such as oscillator 16, must be balanced out by connecting the sensor means 18 across the oscillator 16 in parallel with the cell pairs.

We have found that apparatus as actually constructed according to the teaching of the invention is capable of sensing the very small initial change in impedance resulting from the mere introduction of the contaminant into the specimen cell which change is believed to result in a modification of some sort at the surface of the electrodes of the specimen cell. In any event, referring to the left hand end of the graphs of FIG. 3, it will be seen that an initial decrease in the impedance of the specimen cell (i.e. increase in the ratio of the impedance of the reference cell to the total impedance of the cell pair) is shown at the beginning of the graph in each sector.

Referring to sectors 1 and 2 of FIG. 3, it will be seen that the ratios of the impedances of the specimen cells of the first and second cell pairs to the total impedance thereof are shown as slowly increasing and decreasing about their original values after a period of time. However, sector 3 shows that the ratio of the impedance of the specimen cell of the third cell pair to the total impedance thereof exhibits a relatively radical decrease as indicated by the positive slope of the graph beginning slowly and increasing to a maximum as indicated by the close spaced almost vertical graph portions after which the rate of change becomes less as indicated by the greater slope and spacing of the graph portions.

From the above it will be understood that the apparatus according to this embodiment of the invention is adapted to step the lower boundary of the range of impedance ratios covered by the different sectors of the graph of FIG. 3 associated with each cell pair through successive increments equal to the constant increment of impedance ratios covered by said sectors. The resulting graphical representation as shown in FIG. 3 avoids confusion between the curves generated for the various cell pairs and enables visual analysis and comparison of such curves in a manner similar to the analysis of a fingerprint or "signature".

It will be noted that the graph sectors 6, 7, 11, 14 and 15 all show that the change in impedance ratio of the specimen cell to the total impedance of the cell pairs associated therewith reached a maximum and then began to decrease. Such a result might well represent the inclusion of some antisera in the nutrient media to which the particular micro-organism is sensitive.

However, a further extension of the graph of FIG. 3 in time (i.e., to the right) might also show a cyclical pattern of alternate increases and decreases in impedance ratios for certain cell pairs which is characteristic of the growth pattern for certain micro-organisms. In any event, it will be seen that the apparatus of this invention is capable of substantially simultaneously plotting the growth characteristics of a given micro-organism in a number of different nutrient mediae with and without antisera added thereto and of producing a visible record thereof which can be readily compared with a similar record of the growth of a known micro-organism in the same pattern of nutrient mediae to identify the particular micro-organism.

Obviously, the apparatus can also be used to detect growth of different micro-organisms in the same media as when each specimen cell is inoculated with a blood sample from a different one of a plurality of persons and all of the cells contain the same nutrient media. Of course, in certain applications both the nutrient media of each cell pair and the micro-organism placed in the specimen cell of each cell pair may differ from each other.

It will be understood that the apparatus of this invention could be adapted to successively connect each one of a plurality of specimen cells in series with a single reference cell. It will also be understood that the apparatus could be used to detect impedance changes produced by simple chemical reactions whether or not micro-organisms are involved. Finally, it will be understood that apparatus of the invention could be used to provide impedance ratio measurements between a large number of pairs of fixed impedance elements or between a given fixed impedance element and a sequential series of unknown fixed impedance elements. Thus, it is believed that the apparatus of this invention is quite versatile and will find a wide variety of applications.

In this regard, it will be understood that the digital word output of the apparatus according to the teaching of this invention is suitable for processing by a digital computor and thus through the use of a proper control means, the word itself may be recorded directly, rather than by converting it to an analog signal for recording by means of a strip chart as discussed above. In either case, an important aspect of the apparatus of this invention is that the gain used in making an analysis of its output may be readily changed by simply choosing the number of significant bits of the digital output to be used in the analysis. It will be understood that a very high gain analysis will result if only the least significant bits are utilized in the analysis whereas use of the most significant bits will result in a low gain analysis.

In an actual embodiment of this invention the given signal supplied by the oscillator 16 is about 2KH$_z$ at a voltage of about 100 Millivolts. This embodiment of this invention is capable of sampling two cell pairs per second and of detecting impedance changes of less than one-hundredth of a percent represented by voltage changes in the microvolt range since the digital word output of the apparatus is a 16 bit binary number. Although the use of the digital word output reduces the need for shielding to prevent extraneous responses, the extreme sensitivity of the device, of source, requires appropriate attention to shielding and avoidance of extraneous signals.

Figure 4:
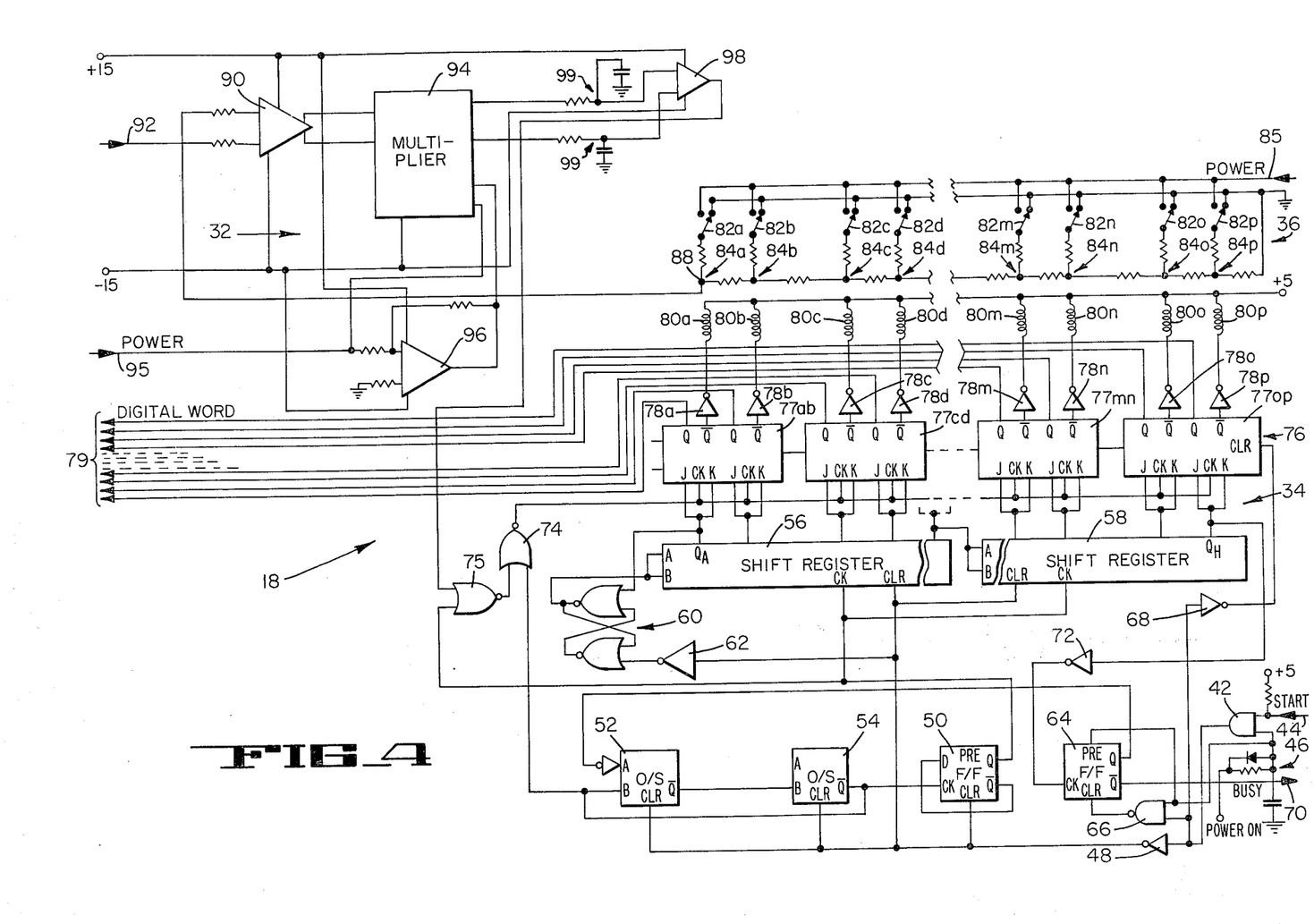
FIGS. 4-7 are schematic diagrams depicting, by way of example only, specific circuits which may be employed in the block diagrams of FIGS. 1 and 2.
Figure 5:
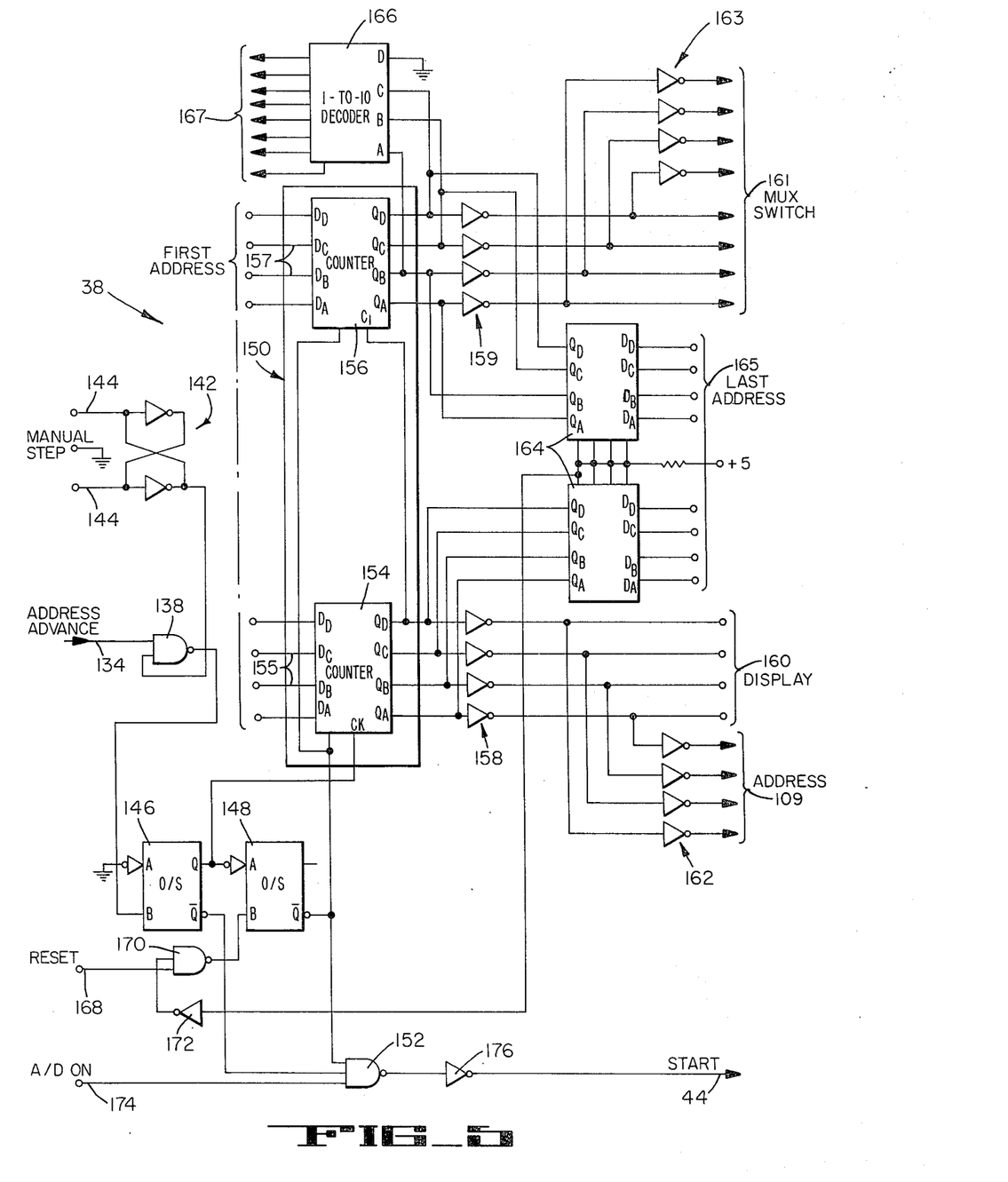
Figure 6:
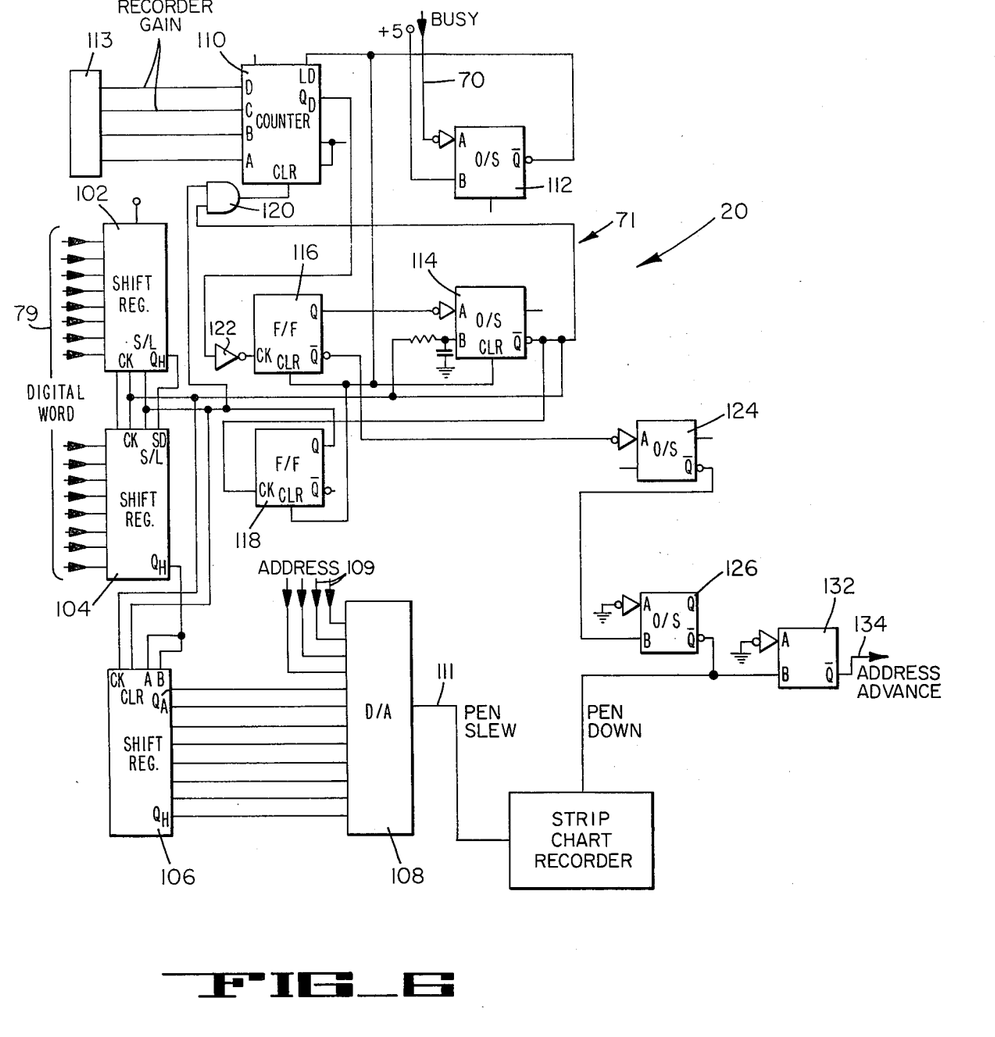
Figure 7:
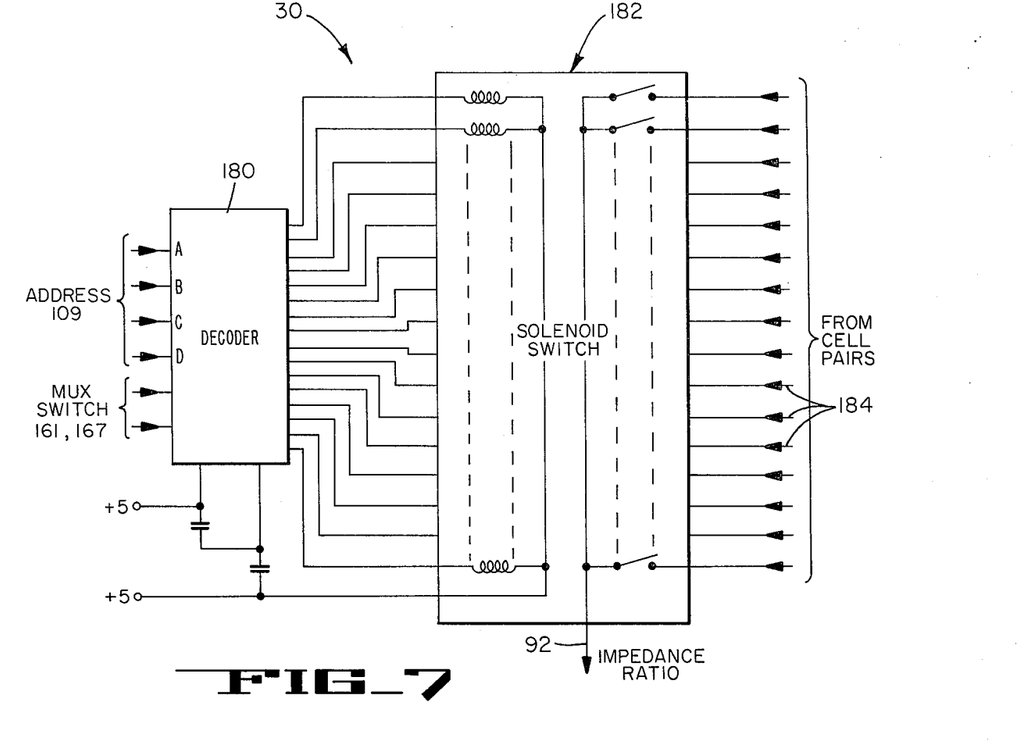

FIGS. 4 through 7 depict, by way of example only, one schematic of the inventive combination shown in FIGS. 1 and 2. FIG. 4 shows the comparator/resistor (sensor) circuit 18 formed of the comparator means 32, the ladder control means 34 and the ladder resistor means 36. Circuit 18 performs an analog-to-digital function, and thus may be termed an analog-to-digital converter means. FIG. 5 shows further details of the logic address circuit 38, while FIG. 6 shows various components of the recorder control means 20. FIG. 7 shows further details of an exemplary multiplex switch means 30.

Referring now to FIGS. 4 through 7 and particularly FIG. 4, the START signal is introduced to one input of AND gate 42 via line 44, and the second input to the AND gate 42 is introduced via a power-on circuit 46 energized via a power-on switch on the front panel (not shown). The output from AND gate 42 is introduced via an inverter 48 to the clear inputs of, a first flip-flop 50, a pair of one-shot multivibrators 52, 54, a pair of serially coupled, (8 bit) shift registers 56, 58 and to an R-S latch 60 via an inverter 62. The output from AND gate 42 is also introduced to a "busy" flip-flop 64 via a NAND gate 66, as well as to an inverter 68. The latter inverter is coupled to the clear input of a register means 76 discussed below. A BUSY output is introduced via line 70 from the flip-flop 64 to a shift control circuit 71 of recorder control means 20, discussed later in FIG. 6.

The power-on circuit 46 also provides a pulse to the second input of NAND gate 66 as well as to the pre-set input of flip-flop 64. The last bit from the shift register 58 is coupled via an inverter 72 to the clock input of the busy flip-flop 64. The Q output of flip-flop 64 is coupled to an input of the one-shot 52 through an inverter. The $\overline{Q}$ output of one-shot 52 is coupled to an input of one-shot 54, whose $\overline{Q}$ output is coupled to the clock input of flip-flop 50, is fed back to the second input of one-shot 52, and is also delivered to one input of a NOR gate 74. The Q output of flip-flop 50 is coupled to the clock inputs of the shift registers 56, 58, and to a NOR gate 75 which is coupled to the second input of the NOR gate 74.

The first bit from the shift register 56 is fed as a second input to the R-S latch 60, whose output is fed into the shift input of the shift register 56. The word outputs from the shift registers 56, 58 are introduced to the JK inputs of the register means 76 which is formed of a series of dual JK flip-flops 77*ab*, 77*cd*, etc. Although only four dual flip-flops are depicted herein for simplicity of presentation, it is understood that there are actually eight dual flip-flops 77 in this circuit embodiment, to thus provide a 16 bit word output. Obviously other pluralities of the various shift registeres, flip-flops, etc. may be utilized depending upon the number of bits desired in the digital word output, the desired apparatus sensitivity, etc.

The plurality of $\overline{Q}$ outputs of dual JK flip-flops 77*a–b–77op* are introduced from the register means 76 via inverters 78*a–78p* to solenoids 80*a–80p* of respective switches 82*a–82p*. The switches 82*a–82p* form part of the ladder resistor means 36 of previous mention, wherein the switches are switches from the normally-closed (NC) contacts to the normally-open (NO) contacts in response to HIGHs introduced from the register means 76. Closure of the switches 82*a–82p* provides coupling of various combinations of the resistors 84*a–84p* of the ladder network 36 in parallel with each other through the NO contacts of the switches 82*a–82p* across the POWER input from the oscillator 16 via the line 85. Thus, the ladder resistor network 36 provides a series of fractions of the voltage of the oscillator 16 at the output 88 thereof, each fraction differing from the next by a small increment as is well known in the digital to analog converter art. It has been found that the use of an R-2R ladder resistor network as shown in FIG. 4 is particularly desirable in the bridge type apparatus of this invention since all of the resistors thereof have only two values and it is much more economical and practical to obtain a plurality of substantially identical resistors than to attempt to obtain sets of matched resistors which vary in value.

The Q outputs of the register means 76 are introduced to the recorder control means 20 via lines 79, as described further in FIG. 6 below. Such Q outputs may also go to a readout display on the front panel of the apparatus (not shown) to provide a momentary display of each digital word as well as of the address.

Regarding now comparator means 32, the output 88 from ladder resistor means 36 is coupled to one input of a differential amplifier 90 of the comparator means 32 and the second input to the differential amplifier 90 is introduced by line 92 from the plurality of cell pairs via the multiplex switch means 30 of FIGS. 2 and 7. The differential outputs of the differential amplifier 90 are in turn coupled to the differential inputs of a four quadrant, complex multiplier 94. The POWER output of the oscillator 16 (FIG. 2) is also introduced via line 95 to a "reference" operational amplifier 96, whose output is fed as the multiplier input to the multiplier 94. The products of the multiplication process of multiplier 94 are introduced through appropriate filter means 99 to a differential comparator 98 whose output is coupled to a second input of the NOR gate 75 in the ladder control means 34. The output from the NOR gate 75 is used as a second inut to NOR gate 74 which serves to apply the clock to the register means 76 in response to an output from differential comparator 98.

Referring now to FIG. 6, the 16 bit word from the register means 76, which represents the approximation of the impedance ratio of a cell pair, is introduced by the lines 79 to the recorder control means 20 and particularly to parallel in/series out shift register 102, 104. The shift registers 102, 104 contents are serially shifted into a series in/parallel out shift register 106 to provide a (8 bit) word, of further description below, which is introduced to respective inputs of digital-to-analog (D/A) converter 108. The ADDRESS word of previous mention in FIG. 2 is also provided to the D/A converter 108 via lines 109 to provide selection of the respective sector of the strip chart in the recorder 22. The D/A converter 108 provides an analog voltage output via terminals 111 to the pen slew of the strip chart recorder 22, which voltage represents the selected fraction of the impedance ratio of the particular cell pair and is recorded on the chart to define one point on the signature chart.

A RECORDER GAIN word is provided to a counter 110 via a presetable thumb-wheel or rotary switch 113. The load input of the counter 110 is coupled to the $\overline{Q}$ output of a one-shot 112, which is also coupled to the clear inputs of a one-shot 114 and flip-flops 116, 118. The BUSY signal of FIG. 4 is introduced to the one-shot 112 via line 70. The one-shot 114 operates as an oscillator circuit and provides an output to the clear input of the counter 110 via an AND gate 120, as well as to the clock inputs of the flip-flop 118 and the shift registers 102, 104 and 106. The Q output of flip-flop 118 is introduced to the second input to AND gate 120, as well as to the shift/load inputs of the shift registers 102, 104 and the clear input of register 106. The $Q_D$ output of the counter 110 is introduced to the clock input of the flip-flop 116 via an inverter 122. The counter 110 is externally set to provide a selected number of shifts in the shift registers 102, 104 via the manually-set rotary switch 113. Thus the word in the shift registers 102, 104 is shifted into the register 106 a number of shifts controlled by the rotary switch setting in response to control by the one-shot 114. Note that the flip-flops 116, 118, one-shots 112, 114 and counter 110 provide the logic shift control circuit 71 of previous mention which determines the timing and selected portion of the 16 bits of the word to be shifted into the D/A converter 108.

The $\overline{Q}$ of flip-flop 116 is coupled to a pen slew delay one-shot 124 which in turn is serially coupled to a pen down one-shot 126. The latter one-shot 126 provides an ADDRESS ADVANCE signal via line 134 through serially connected address delay one-shot 132. The ADDRESS ADVANCE signal is introduced to the logic address circuit 38 of FIG. 5 to provide an output pulse for incrementing by one the address introduced to the D/A converter 108 and to the multiplex switch 30.

The pen slew one-shot 124 provides a suitable delay for preventing dragging the pend during its movement across the chart, since the D/A converter 108 operates much more rapidly than the pen can move across the chart, and the pen down one-shot 126 holds the pen down for a selected interval of time. The address delay one-shot 132 prevents dragging of the pen when the system is incremented.

Referring again to FIG. 5, there is shown in greater detail the logic address circuit 38 of previous mention. The ADDRESS ADVANCE signal on line 134 from FIG. 4, is introduced to a NAND gate 138 which has a second input thereto from a latch 142. The latter is coupled to a front panel push button (not shown) via input lines 144. Each time the push button is closed it generates a single (step) pulse, which manually performs the same function as does the ADDRESS ADVANCE from the recorder control means 20. NAND gate 138 in turn is coupled to a one-shot 146, whose Q output is coupled to a one-shot 148, as well as to the clock input to address register means 150 formed of a pair of counters 154, 156. The $\overline{Q}$ output of one-shot 146 and the $\overline{Q}$ output of one-shot 148, are coupled as inputs to a NAND gate 152. One-shot 148 has $\overline{Q}$ coupled to the load inputs of the counters 154, 156. A FIRST ADDRESS word is provided to the counters 154, 156. from a plurality of switches located on the front panel (not shown) via input terminals 155, 157. The Q outputs of the counter 154 are coupled to conventional display indicator lights (not shown) via inverters 158 and terminals 160. The outputs from inverters 158 are also coupled to inverters 162 to provide the ADDRESS via lines 109 to the multiplex switch means 30 (FIG. 7), as well as to the D/A converter 108.

The Q outputs of counter 156 are coupled as a MUX SWITCH signal to the inputs of the multiplex switch means 30 (FIG. 7) via inverters 159, inverters 163 and lines 161. In addition, the Q outputs from the counters 154, 156 are coupled to comparator means 164 formed, for example, of a pair of comparators, wherein terminals 165 provide input of a LAST ADDRESS word introduced via manually-set switches on the front panel (not shown). Three of the Q outputs of counter 156 are also coupled to a 1-to-10 line decoder 166 whose output lines 167 are fed, along with the outputs from the inverters 159, 163, to the multiplex switch means 30, to provide selective sequencing of the switch means 30. Note that the number of output lines 161, 167 shown here are sufficient to handle a multiplex switch 30 capable of stepping through, for example, 64 cell pairs, although only three cell pairs are shown in FIG. 2.

A RESET pulse is introduced via terminal 168 as one input to a NAND gate 170, while the combined output from the comparators of comparator means 164 is introduced as the other input to NAND gate 170 via an inverter 172. NAND gate 170 is coupled to the input of the one-shot 148. The third input to NAND gate 152 is provided via input terminal 174 from an A/D on switch on the front panel (not shown). The output of NAND gate 152 provides the START pulse via line 44 to the comparator/resistor (sensor) circuit 18 (FIG. 4) via an inverter 176. The push button coupled to input 174 starts the A/D converter 108 via the START signal.

In operation, referring to the invention combination of FIGS. 4 through 7, a selected number of cell pairs 24–28 (FIG. 2) containing specific combinations of nutrient mediae and micro-biological contaminants, are plugged into the apparatus as described, for example, in the above-mentioned U.S. Pat. No. 3,743,581. In addition, the various manual settings are selected to provide external control of the apparatus in accordance with the number and location of cell pairs being used; the number and position of the records on the strip recorder; the time duration of the measurements; the number of shifts made on the 16 bit word; etc. Thus, the rotary switch 113 is set in accordance with the number of shifts desired for the word in the shift registers 102, 104; the FIRST ADDRESS and LAST ADDRESS inputs to the address register means 150 and the decoder means 164, respectively, are set in accordance with the number and positions of the cell pairs; etc.

When the apparatus is ready for operation, the power-on circuit 46 (FIG. 4) is energized, thereby initiating (CLEAR) pulses which are introduced to all the one-shots 52, 54, flip-flops 50, 64 and registers 56, 58 and 76, in order to set all logic devices to the desired initial state. When the power-on circuit 46 is turned on, the capacitor thereof charges to 5 volts via the RC circuit, which maintains the flip-flop 64 in reset condition to prevent circuit oscillations for the first fraction of a second after turn-on.

The A/D on switch (not shown) is also turned on to provide a HIGH via input 174 of FIG. 5 which, in turn, provides the initial START pulse via line 44 to the ladder control means 34 of FIG. 4. Manually energizing the A/D on, manual step, or reset switches (input terminals 174, 144, 168, respectively of FIG. 5) also generates a START signal in the form of a negative pulse or LOW which is introduced to the various one-shots, flip-flops and registers, to clear these components while setting the latch 60. Thus, the system generally is started by the START pulse on line 44 of the ladder control means 34, which in turn can be generated manually or automatically during a measurement cycle, via the various inputs 134, 144, 168, 174.

The START pulse sets the flip-flop 64, whereby the Q̄ output therefrom provides a BUSY signal which is delivered to the A input of the one-shot 112 in the shift control circuit 71 (FIG. 6) to initiate operation of the shift logic; i.e., to load the recorder gain setting on the rotary switch 113 into counter 110. The START pulse is also introduced to the clear inputs of the dual JK flip-flops 77 which form the register means 76. START fed to flip-flop 64 fires the one-shot 52, which in turn fires the one-shot 54. The latter's Q̄ output is accordingly delayed by a pulse width which is equal to the duration of the one-shot 52 pulse. The delayed pulse in turn sets the flip-flop 50 on the positive going edge, whereupon the flip-flop 64 remains set until the next START pulse. The flip-flop 50 introduces a clock pulse to the clock inputs of the serially-coupled shift registers 56, 58 as well as to the NOR gate 75.

The START pulse sets the latch 60 via inverter 62, which provides the serial input to the shift register 56. The latter generates a HIGH as the first bit of the register means 76, which is fed back to clear the latch 60. Thus the HIGH, or 1, is shifted down the shift registers 56, 58 by the clock from the flip-flop 50, to provide successive actuation of the switches 82a via the solenoids 80a–80p. For example, the first resistor 84a of the ladder resister means 36 is placed in the circuit, whereby an analog voltage signal is introduced via terminal 88 to the input of the differential amplifier 90. Amplifier 90 performs the function of taking the difference between the analog voltage from the ladder resistor means 36 and the analog voltage introduced via line 92 from the particular cell pair 24–28, etc., which is in the circuit. The voltage from the cell pair is representative of the impedance ratio between the cells. The outputs from the differential amplifier 90 are in turn introduced to the multiplier 94. Simultaneously, the output of the referenced operational amplifier 96 is introduced to the multiplier 94, whereupon the outputs of the differential amplifier 90, representing the impedance ratio of the cell pairs, are multiplied by the output of the reference operation amplifier 96. The products of the multiplication are introduced from the multiplier 94 to the differential comparator 98 which provides either a HIGH (1) or LOW (0) output state. The states represent whether the impedance ratio of the cell pair is above or below the fractional voltage provided at output 88 of the ladder network. The digital state of the differential comparator 98 output is introduced via the NOR gates 75, 74 to the clock inputs of the register means 76. If the differential comparator output is HIGH, the first bit of the word being generated at the Q outputs of the register means 76 is a 1, which appears at the output terminals 79 as the first bit of the word being introduced to the shift registers 102, 104 of the recorder control means 20 (FIG. 6). If the differential comparator 98 output is a LOW, the register means 76 outputs a 0 as the first digit of the digital word.

The process is repeated each time the 1 is stepped down the shift registers 56, 58, with an added resistor (84a–84p) being placed in the circuit for comparison with the impedance ratio (voltage) appearing at the cell pair output (92). The resulting (16 bit) digital word generated at the Q outputs of register means 76 is an approximation of the impedance ratio of the cell pair at that time of measurement. The plurality of bits forming the (16 bit) word introduced to the shift registers 102, 104 of the recorder control means 20, are generated during (16) consecutive cycles of the process which steps the ladder switches 82a–82p down the resistors 84a–84p. The final digital word thus actually represents the voltage level of the single point representing the impedance ratio of the respective cell pair being measured.

It may be seen that the approximation process employing the ladder resistor means 36 successively divides by half the voltage value (width of the corresponding sector of strip chart) remaining after the previous approximation. For example, the first approximation determines whether the true value is more or less than one-half. If the value is more, the first bit of the register means 76 (the Q output) is a 1. If less, the output is a 0. Next, the circuit determines whether the value is more or less than the first 1 (i.e. one-fourth) plus the next fraction (i.e. one-eighth) etc., and corresponding digital states are generated until the 16 divisions by half are made. The resulting digital word is placed in the shift registers 102–106, and the corresponding analog level is recorded in the recorder means 22 via the D/A converter 108.

When the digital word is completed, and is utilized in the recorder control means 20 of FIG. 6 to record a single point on the strip chart recorder of recorder means 22, a HIGH is introduced from the last bit of the shift register 58 to the clock input of flip-flop 64 via inverter 72. The HIGH clears the latter flip-flop to prepare it for another START pulse, while providing a HIGH to the one-shot 52 to inhibit the latter. The one-shots 52, 54 act as an oscillator loop, which in combination with flip-flop 50 provide square waves of half the oscillator loop rate to define CLOCK for stepping the 1 down the shift registers 56, 58. As noted, the first 1 comes from latch 60. After clearing the latch 60 the 1 is clocked down the shift registers 56, 58 until the last bit, whereupon the one-shot 52 is inhibited. The START pulse clears the word out of the register means 76 and the shift registers 56, 58 to thus set the busy flip-flop 64 again to provide the BUSY signal via line 70, and thus start the next measurement cycle. The BUSY signal is introduced to the recorder control means 20 which subsequently provides the ADDRESS ADVANCE pulse to the logic address circuit 38 via line 134. The latter circuit 38 then provides the ADDRESS word via lines 109 to the address inputs of the D/A converter 108, and also to the address inputs of the multiplex switch means 30, to provide selection of the next cell pair for the next measurement cycle as well as to provide selection of the respective sector of the strip chart on the recorder 22. The operation of the circuits 20, 38 and 30 of FIGS. 5, 6 and 7 is further described below.

Referring to FIG. 6, the shift control circuit 71 provides logic for selecting and controlling the number of shifts performed on the digital word in the shift registers 102, 104. The number of shifts is entered via the rotary switch 113. The shift operation is performed in response to the BUSY pulse fed to one-shot 112 which in turn, sends a LOAD pulse to the counter 110 and a CLEAR pulse to the one-shot 114 and flip-flops 116, 118. The one-shot 114, coupled to one-shot 112, acts as an oscillator and is coupled as a feedback loop to the counter 110 to generate the pulses that are counted. The first pulse is not counted but is used to load the digital word into the shift registers 102, 104. Thus, if the rotary switch 113 is set at the number 8, the shift control circuit 71 generates one load pulse and eight shift pulses. This provides an eight digit shift of the (16 bit) word in the shift registers 102, 104, which generates an 8 bit word from the least significant bits of the 16 bit word. This provides sufficient gain to allow detection of minute impedance ratio changes. Flip-flop 118 determines whether the shift registers 102, 104 are loading or shifting and is clocked at a rate determined by the one-shot 114. In response to the clock, the (8 bit) word is shifted from the resistor 102 to the D/A converter 108. The resulting analog voltage corresponding to the sum of the impedance ratio voltage of the cell pair and the address voltage thereof is introduced via line 111 to control the lateral position of the pen apparatus within the chart width of the strip chart recorder. The specific sector is selected via the ADDRESS word introduced to the D/A converter 108 and the voltage level corresponding to the impedance ratio is recorded as a single point on that sector.

More particularly, the $\overline{Q}$ output provides a LOW from flip-flop 116 to the pen-slew delay one-shot 124, which provides sufficient delay to allow the pen to mechanically move across the chart and stabilize in the position corresponding to the voltage level. In turn, the pen-down one-shot 126 receives the output from the one-shot 124 and provides suitable time for allowing the pen to move down and make its mark. The address one-shot 132 provides suitable delay before movement of the strip chart, thereby preventing the pen from dragging on the strip chart. The $\overline{Q}$ output from one-shot 132 provides the ADDRESS ADVANCE signal via output 134 for introduction to the logic address circuit 38 of FIG. 5, after the analog voltage corresponding to the previous impedance ratio has been recorded by the pen.

Referring in addition to FIG. 5, the input ADDRESS ADVANCE automatically provides a START signal after a measurement cycle via the components 138, 146, 148, 152. The ADDRESS ADVANCE input can also be manually initiated via the MANUAL STEP inputs 144 and the NOR latch 142. ADDRESS ADVANCE is introduced to the one-shot 146 to provide a LOW to the NAND gate 152. In response to the input via NAND gate 170, a LOW is delivered from the one-shot 148 to the NAND gate 152. Thus the START pulse may be regenerated manually for a particular cell by the reset means 168.

To provide selection of the cell pair, the ADDRESS ADVANCE pulse triggers one-shot 146, which provides a HIGH to clock the counters 154, 156. If the binary number set by the LAST ADDRESS word input to address register 150 matches the binary number input to the comparator 164, then the combined output from comparator 164 goes HIGH (e.g., to 5 volts) which enables the one-shot 148 via NAND gate 170. Then the one-shot 148 is triggered and the FIRST ADDRESS word is loaded via terminals 155, 157 into counters 154, 156, and the cell pair selection sequence is repeated during the next measurement cycle.

The DISPLAY word is employed via terminals 160 to indicate the cell pair being sampled, the first and last cell pairs being determined by the inputs to the counters 154, 156 and the comparator 164 respectively.

FIG. 7 depicts, by way of example only, an embodiment of the multiplex switch means 30. A decoder 180 receives the ADDRESS word via lines 109, and the MUX SWITCH word via lines 161, 167. The decoder 180 is coupled to a solenoid switch 182 whereby selected switch contacts are energized to couple a selected cell pair 24–28, etc., via lines 184, to the comparator means 32 via line 92 (FIG. 4). The desired cell pair is selected by energizing a solenoid to close the respective contact in the solenoid switch 182 associated with the cell pair.

Figure 8:
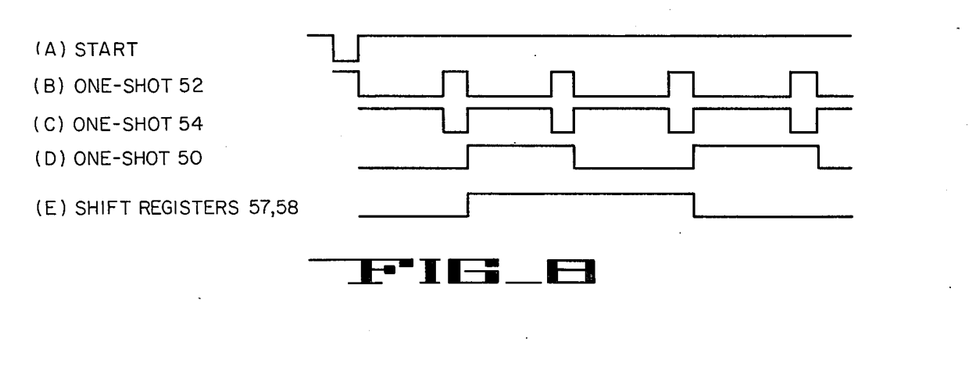
FIG. 8 is a graph of a series of waveforms depicting the operation of the invention at specific points therealong.

FIG. 8A–E depicts a series of waveforms generated at various points along the ladder control means 34 of FIG. 4. FIG. 8A shows the START pulse introduced via line 44. FIG. 8B depicts the high generated via $\overline{Q}$ of the one-shot 52, while FIG. 8C shows the LOW from $\overline{Q}$ of one-shot 54. FIG. 8D depicts the HIGH generated via flip-flop 50 and which is used, along with the LOW from one-shot 54, to enable the NOR gates 75, 74 to clock the register means 76. FIG. 8E depicts the resulting $Q_4$ output from the first bit of the shift register 56, i.e., the 1 bit which is stepped down the registers 56, 58.

Obviously, there are many alternative circuits and modifications for the circuits exemplified in FIGS. 4 through 7 by way of example only. The ladder control means 34 may be replaced with a pair of integrated circuits commonly termed "successive approximation registers". The latter would provide buffered inputs to the switch solenoids 80a–80p to close contacts 82a–82p, by the additional modification of adding inverters to the successive approximation register outputs.

What is claimed is:

1. Apparatus for assessing growth of micro-organisms comprising:

a. means for supplying an electrical reference signal;
b. a pair of cells including a reference cell and a specimen cell each of which contains a sample of the same nutrient media while the specimen cell further contains a selected micro-organism contaminant, each cell of said pair of cells including a pair of spaced electrodes in contact with said nutrient media contained therein and said cells being connected in series with each other across said means for supplying an electrical reference signal; and
c. sensor means connected across said means for supplying an electrical signal in parallel with said series connected pair of cells and including means connected to the junction between said series connected pair of cells for generating an electrical signal in the form of one of a finite number of digital words each including a given number of digits, which digital word is representative of the electrical impedance ratio between said series connected pair of cells, said finite number of digital words being larger than said given number of digits.

2. Apparatus as claimed in claim 1 wherein said sensor means comprises means for providing a series of fractions of said electrical reference signal differing from each other by small increments at a first output terminal and a corresponding series of digital words each representative of a different one of said series of fractions at other output terminals thereof, and a voltage comparator having one input connected to said first output terminal and a second input connected to the junction between said series connected pair of cells, the output of said voltage comparator being connected to cancel at said other output terminals all digital bits of said series of digital words representative of a fraction of said electrical reference signal greater than the fraction of said electrical reference signal present at said junction between said series connected pair of cells.

3. Apparatus as claimed in claim 1 comprising a plurality of said pair of cells connected in parallel with each other across said means for supplying an electrical reference signal and wherein said sensor means includes a multiplex switch means for selectively connecting the junction between each series connected pair of cells of said plurality of said pair of cells to said sensor means in turn.

4. Apparatus as claimed in claim 3 including recorder means for making a record of at least a part of each digital word representative of the electrical impedance ratio between each of said series connected pair of cells of said plurality of said pair of cells.

5. Apparatus as claimed in claim 4 including a logic address means for selectively operating said multiplex switch means to connect the junction between the selected series connected pair of cells of said plurality of said pair of cells to said sensor means and simultaneously generating a digital word indicative of said selected series connected pair of cells, and means connecting said logic address means to said recorder means for recording of said digital word indicative of said selected series connected pair of cells by said recorder means with said record of at least part of the digital word representative of the electrical impedance ratio between the cells of said selected series connected pair of cells.

6. Apparatus as claimed in claim 5 wherein said recorder means includes control means connected to said logic address means for causing said logic address means to advance said multiplex switch means from one position thereof to the next.

7. Apparatus as claimed in claim 6 wherein said recorder means includes a strip chart recorder and said control means includes digital to analog converter means connected to said sensor means for converting at least a portion of each word of said series of digital words representative of said series of fractions to an analog voltage representative thereof and digital to analog converter means connected to said logic address means for converting said digital word indicative of said selected series connected pair of cells to an analog voltage representative thereof.

8. Apparatus as claimed in claim 7 wherein said control means includes means for combining said analog voltages from said digital to analog converter means thereof for application to said strip chart recorder and delay means for controlling operation of said strip chart recorder after application thereto of said combined analog voltage representative of said combination of said digital words and before operation of said logic address means to advance siad multiplex switch.

9. Apparatus as claimed in claim 8 wherein said control means includes an adjustable counter means interposed between said digital to analog converter means thereof and said sensor means, said adjustable counter means being adapted to control the number of significant bits of said digital words representative of said series of fractions which are applied to said digital to analog converter means.

10. Apparatus as claimed in claim 9 wherein said electrical reference signal has a frequency between about 10 $H_z$ and about 100 $KH_z$ and a voltage between about 100 millivolts and 1,000 millivolts and said voltage comparator of said sensor means includes means for multiplying both the fractions of said electrical reference signal provided by said sensor means and the fractions of said electrical reference signal present at the junction between each series connected pair of cells of said plurality of said pair of cells by said electrical reference signal.

11. An automated bridge circuit for measuring the ratio of the impedance of one of a pair of impedance elements to the total impedance of said pair of impedance elements comprising:
a. means for supplying an electrical reference signal;
b. means for connecting said pair of impedance elements in series with each other across said means for supplying said electrical reference signal;
c. sensor means connected across said means for supplying said electrical reference signal in parallel with said means for series connecting said pair of impedance elements, said sensor means including means for connection to the junction between said series connected pair of impedance elements for generating an electrical signal in the form of one of a finite number of digital words each including a given number of digits, which digital word is representative of the ratio of the impedance of said one of said pair of impedance elements to the total impedance of said pair of impedance elements and said finite number of digital words being larger than said given number of digits.

12. An automated bridge circuit as claimed in claim 11 wherein said sensor means comprises a network of fixed impedance elements for producing an output in the form of a series of fractions of said electrical reference signal differing from each other by small increments under the control of a control circuit which produces a corresponding series of digital words each representative of a different one of said series of fractions as an electrical output thereof, a voltage comparator having one input connected to said output of said network of fixed impedance elements and a second input connected to the junction between said series connected pair of impedance elements, the output of said voltage comparator being connected to said control circuit to cause cancellation of any bit of said series of digital words representing a fraction of said electrical reference signal present at said one input of said voltage comparator which is greater than said fraction of said electrical reference signal present at said second input of said voltage comparator.

13. An automated bridge circuit as claimed in claim 11 wherein said network of fixed impedance elements comprises an R-2R ladder network of fixed resistor elements, each leg of said R-2R ladder network includes a solenoid operated mechanical switch, said control circuit includes a shift register for selectively energizing the solenoid of each solenoid operated switch together with means for providing an electrical output in the form of a digital word having a different bit corresponding to the solenoid of each solenoid operated switch, and the output of said comparator is connected to said shift register to de-energize any solenoid, the energization of which results in a fraction of said reference signal at said first input thereof which is greater than the fraction of said reference signal of said second input thereof.

14. An automated bridge circuit as claimed in claim 13 wherein said means connected to the junction between said series connected pair of impedance elements includes a multiplex switch means whereby connection may be made to each of a plurality of junctions between each of a plurality of pairs of impedance elements in turn.

15. An automated bridge circuit as claimed in claim 14 including display means providing a visual presentation of at least a part of each digital word representative of the electrical impedance ratio between each pair of said plurality of pairs of impedance elements.

16. An automated bridge as claimed in claim 15 including a logic address means for selectively operating said multiplex switch means to connect the junction between a selected pair of impedance elements to said sensor means and simultaneously generating a digital word indicative of said selected pair of impedance elements, and means connecting said logic address means to said display means whereby said digital word indicative of said selected pair of impedance elements is visually displayed by said display means together with said at least part of said digital word representative of the electrical impedance ratio between the elements of said selected pair of impedance elements.

17. An automated bridge as claimed in claim 16 including control means connected to said logic address means for causing said logic address means to advance said multiplex switch means from one position thereof to the next.

18. An automated bridge as claimed in claim 17 including recorder means for providing a record of at least a part of each digital word representative of the electrical impedance ratio between the elements of each of said plurality of pairs of impedance elements.

19. An automated bridge as claimed in claim 18 wherein said control means includes first digital to analog converter means connected to said sensor means for converting at least a portion of each digital word representative of the electrical impedance ratio between the elements of each of said plurality of pairs of impedance elements to a first analog voltage and second digital to analog converter means connected to said logic address means for converting said digital words indicative of the selected pair of impedance elements to a second analog voltage.

20. An automated bridge as claimed in claim 19 wherein said recorder means is a strip chart recorder and said control means includes means for combining said first and second voltages for recording by said strip chart recorder and adjustable counter means interposed between said first digital to analog converter means and said sensor means, said adjustable counter means being adapted to control the number of significant bits of said digital words representative of the electrical impedance ratio between the elements of each of said plurality of pairs of impedance elements which are applied to said first digital to analog converter means.

21. An automated bridge circuit as defined in claim 11 wherein said pair of impedance elements is a pair of cells including a reference cell for containing a sample of nutrient media and a sample cell for containing a sample of nutrient media and a selected micro-organism contaminant, each cell of said pair including a pair of spaced electrodes for contact with said nutrient media when contained therein.

* * * * *